United States Patent [19]

Büssemeier et al.

[11] 4,455,395
[45] Jun. 19, 1984

[54] PROCESS FOR THE PRODUCTION OF UNSATURATED HYDRO-CARBONS

[75] Inventors: Bernd Büssemeier, Mülheim; Carl D. Frohning; Gerhardt Horn, both of Oberhausen; Werner Kluy, Bochum-Stiepel, all of Fed. Rep. of Germany

[73] Assignee: Ruhrchemie Aktiengesellschaft, Fed. Rep. of Germany

[21] Appl. No.: 409,888

[22] Filed: Aug. 20, 1982

Related U.S. Application Data

[63] Continuation of Ser. No. 308,609, Oct. 5, 1981, abandoned, which is a continuation of Ser. No. 6,870, Jan. 26, 1979, abandoned, which is a continuation of Ser. No. 821,206, Aug. 2, 1977, abandoned, which is a continuation of Ser. No. 679,141, Apr. 22, 1976, abandoned.

[30] Foreign Application Priority Data

Apr. 29, 1975 [DE] Fed. Rep. of Germany ....... 2518964

[51] Int. Cl.$^3$ ................................................ C07C 1/04
[52] U.S. Cl. ................................... 518/717; 518/721; 502/324
[58] Field of Search ................................ 518/717, 721

[56] References Cited

U.S. PATENT DOCUMENTS 2,778,845  1/1957  McGrath .
2,960,518  11/1960  Peters .
2,973,384  2/1961  Hayashi .

Primary Examiner—Howard T. Mars
Attorney, Agent, or Firm—Jordan B. Bierman; Linda Bierman

[57] ABSTRACT

In a process for the production of unsaturated hydrocarbons comprising catalytic conversion of a feed gas comprising carbon oxides and hydrogen, the improvement which comprises carrying out said conversion at a temperature of 250° to 350° C. and under a pressure of 10 to 30 bars, said catalyst comprising at least one difficultly reducible oxide of the transition metals of Groups V and/or VII of the Periodic Table combined with at least one metal of Group 8 of the Periodic Table.

7 Claims, No Drawings

PROCESS FOR THE PRODUCTION OF UNSATURATED HYDRO-CARBONS

This is a Rule 60 Continuation of Ser. No. 308,609, filed Oct. 5, 1981 now abandoned, which is a Rule 60 Continuation of Ser. No. 006,870, filed Jan. 26, 1979 now abandoned, which is a Rule 60 Continuation of Ser. No. 821,206, filed Aug. 2, 1977 now abandoned, which is a Rule 60 Continuation of Ser. No. 679,141 now abandoned, filed Apr. 22, 1976, which, in turn, claims the priority of German Application No. P 25 18 964.4, filed Apr. 29, 1975.

The present invention is directed to an improvement in the process for the production of unsaturated hydrocarbons by reacting carbon oxides with hydrogen in the presence of a catalyst.

German Pat. No. 922,833, for example, discloses a process for the production of unsaturated hydrocarbons based upon the reaction of carbon monoxide with hydrogen in the presence of a finely divided fused iron catalyst. In this process, which is especially adapted for the production of gaseous hydrocarbons, the catalyst is periodically or continuously removed from the reaction chamber, regenerated, reduced, and returned. The reaction is carried out under atmospheric or slightly elevated pressure and at temperatures above about 450° C. It is most preferable to operate between 470° and 600° C.

In another process (described in German Pat. No. 896,338), unsaturated gaseous hydrocarbons are produced by reacting carbon monoxide with hydrogen in the presence of stable oxides of metals of Groups II to VII of the Periodic Table. The reaction is carried out at about atmospheric pressure at temperatures in excess of 520° C.

It is noted that the comparatively high reaction temperatures used in the prior art processes result in the formation of substantial quantities of carbon from the carbon monoxide. This is in accordance with the Boudouard equilibrium. The carbon produced in the course of these reactions deposits on the surface of the catalyst being used and causes deactivation thereof. In some cases, there is actual disruption of the catalyst structure which considerably reduces the catalyst life.

In another prior art process, catalysts comprising at least 98% by weight of a support and from 0.3 to 2% by weight of cobalt, nickel, or platinum are used for the production of ethylene by conversion of a mixture of carbon monoxide and hydrogen. This process is described more completely in DAS No. 1,271,098. The reaction calls for a throughput rate of 2500 to 3000 liters of gas per liter of catalyst per hour at a temperature of 300° to 450° C. and at pressure of 130 to 200 mm. of mercury. This process is characterized by its ability to produce substantial percentages of the lower gaseous olefins. However, the conversion rates which can be achieved are in the order of 10 to 20%. These are quite low and are generally considered to be unsatisfactory.

When hydrogenating carbon oxides, the conversion rate is greatly dependent upon the partial pressure of the hydrogen. The greater this partial pressure, the higher the conversion rate which will be achieved. However, there is a negative aspect of this relationship. This same high partial pressure also causes hydrogenation of the olefins formed to produce the saturated, rather than unsaturated, hydrocarbons.

Therefore, if olefinic hydrocarbons are desired, it is necessary to adjust the hydrogen partial pressure or the synthesis pressure so that the hydrogenation of carbon oxides proceeds at a great rate while, at the same time, the undesired hydrogenation of the olefins is largely suppressed.

In practicing the present invention, it has been found that unsaturated hydrocarbons, especially gaseous olefins, are obtained in high yields from the catalytic conversion of carbon oxides and hydrogen at elevated temperatures and pressures. The reaction should be carried out at about 250° to 350° C. and about 10 to 30 bars pressure. The catalyst used should contain oxides of Groups V and/or VII of the Periodic Table which are difficult to reduce. These oxides should be used in combination with at least one metal of Group VIII of the Periodic Table.

The catalysts useful in the present process are produced in a known manner. Compounds which are capable of being converted to their corresponding stable oxides at the reaction temperature may be used in place of the oxides of the transition metals of Groups V and VII: As a result, it is possible to obtain the catalysts by precipitating the constituents from their aqueous solutions by means of suitable precipitating reagents, such as alkali metal carbonates. An alternative process for the production of the catalysts comprises mixing the constituents, homogenizing the mixture, and shaping it mechanically. In addition, the catalyst may also be obtained by sintering the constituents themselves.

It has been found advantageous to include promoters such as alkali metal carbonates, magnesium oxide, or zinc oxide in the catalysts. These increase the activity and the yield. Carriers such as precipitated or natural silicic acid, kieselguhr, aluminum oxides, aluminum oxyhydrates, and natural and synthetic silicates such as magnesium silicate, aluminum silicate, or pumice may also advantageously included in the catalysts.

Oxides of vanadium and/or manganese and/or rhenium have been found especially suitable as the stable oxides which are reducable only with difficulty. Iron and cobalt are preferred for the metals of Group VIII. Especially advantageous is a catalyst comprising 50 to 100 parts of vanadium, 3 to 5 parts of $K_2O$ and 5 to 15 parts of zinc oxide per 100 parts by weight of iron.

Before being contacted with the feed gas, the catalysts are reduced with hydrogen. During this reduction, it is preferred to maintain temperatures of approximately 350° to 520° C. and pressures of about 1 bar. The catalysts are generally used in the form of a stationary bed, although they may also be used in finally divided form. In the latter case, a whirling motion is imparted to them by the gas flowing through the reaction space. The catalysts may be withdrawn from the reaction vessel either continuously or intermittently for regeneration. This is accomplished by burning off the contaminants adhering to the catalyst in air in a separate vessel.

The operation of the present process is quite simple. The feed gas comprising carbon monoxide and hydrogen is passed over the catalyst in a pressure reactor at an inlet temperature of about 300° C. The ratio of carbon monoxide to hydrogen in the feed gas is usefully 2:1 to 1:2. These ratios are not essential to the opertion of the process, but have been found to be advantageous. Most preferred are those mixtures which contain a slight excess of carbon monoxide. The gas mixture, after leaving the reactor is then treated in a known manner to remove the desired unsaturated gaseous hydrocarbons produced. The mixture is then returned to the reactor inlet for further processing.

It has been found that the total conversion of carbon monoxide and hydrogen in the present process is from 80 to 90%. At least 60 to 70% of the reaction products is $C_2$ to $C_4$ olefins.

EXAMPLE 1

A catalyst according to the present invention was prepared by homogenizing a mixture of iron oxide (e.g., $Fe_2O_3$, zinc oxide and $Fe_3O_4$), vanadium oxide (e.g., $V_2O_5$) and potassium carbonate. The ratio was 100 parts by weight of iron, 70 parts by weight of vanadium, 10 parts by weight of zinc oxide and 4 parts by weight of $K_2O$. After molding and sintering of the mixture at 1050° C., the catalyst was reduced for several hours at 500° C.

A 30 cm. deep layer of the foregoing catalyst was charged into a test furnace 1 m. in length and 10 mm. in inside diameter. The reactor was brought to the reaction temperature by an electric heater. A mixture of carbon monoxide and hydrogen, having a molar ratio of 1:1, was then passed over the catalyst at a space velocity of 500 standard liters of gas mixture per liter of catalyst per hour. This was carried out at a temperature of 320° C. and a pressure of 10 bars. The conversion of carbon monoxide and hydrogen was a total of 85% and the yield was 152 grams. The composition of the reaction product was as follows:

| | |
|---|---|
| $C_2H_4$ | 26.1% by weight |
| $C_3H_6$ | 18.6% by weight |
| $C_4H_8$ | 14.4% by weight |
| $C_2-C_4$, saturated | 13.2% by weight |
| Total | 72.3% by weight |

The proportion of methane was 12% by weight and the balance was hydrocarbons having more than 4 carbon atoms.

EXAMPLE 2

The process was carried out in accordance with Example 1 except that the catalyst comprised 100 parts by weight of iron, 100 parts by weight of manganese, 10 parts by weight of zinc oxide and 4 parts by weight of $K_2O$. The conversion of carbon monoxide and hydrogen was 86% and the yield was 164 grams. The reaction product contained the following:

| | |
|---|---|
| $C_2-C_4$ | 31.3% by weight |
| $C_3H_6$ | 22.2% by weight |
| $C_4H_8$ | 17.4% by weight |
| $C_2-C_4$, saturated | 15.7% by weight |
| Total | 86.6% by weight |

In addition, 9.6% by weight of methane was obtained and the balance was hydrocarbons having more than 4 carbon atoms.

The operable elements or oxides of Groups V and/or VII are as follows: vanadium, niobium, tantalum, manganese, technetium, rhenium.

The term carbon oxides means carbon monoxide, carbon dioxide and mixtures of these.

What is claimed is:

1. In a process for the production of hydrocarbon mixtures containing predominantly olefins comprising catalytic conversion of a feed gas comprising carbon oxides and hydrogen in the presence of a catalyst containing iron and those oxides of vanadium and/or manganese which are difficult to reduce at elevated temperatures and pressures, the improvement which comprises carrying out said conversion at a temperature of 250° C. to 350° C. and under a pressure of 10 to 30 bars, in the presence of a catalyst consisting essentially of 100 parts by weight of iron, and 50 to 100 parts by weight of an oxide of manganese and/or vanadium, said oxide being difficult to reduce, said catalyst including 3 to 5 parts by weight of $K_2O$, and 5 to 15 parts by weight of ZnO.

2. The process according to claim 1 wherein said oxide is of manganese.

3. The process of claim 1 wherein said catalyst further comprises at least one carrier.

4. The process according to claim 1 wherein there is a carrier present selected from the group consisting of silicic acid, kieselguhr, aluminum oxides, aluminum oxyhydrate, and silicates.

5. The process according to claim 1 wherein magnesium oxide is present as an additional promoter.

6. The process of claim 1 wherein said olefins contain 2 to 4 carbon atoms.

7. The process according to claim 4 wherein said silicates are selected from magnesium silicate, aluminum silicate, or pumice.

* * * * *